United States Patent
Blaustein et al.

(12) 
(10) Patent No.: US 6,189,693 B1
(45) Date of Patent: *Feb. 20, 2001

(54) ELECTRIC TOOTHBRUSH

(75) Inventors: Lawrence A. Blaustein; John Osher, both of Moreland Hills; John R. Nottingham, Hunting Valley; John W. Spirk, Gates Mills, all of OH (US)

(73) Assignee: Dr. Johns Products, Ltd., Bedford Heights, OH (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/236,794

(22) Filed: Jan. 25, 1999

Related U.S. Application Data

(63) Continuation-in-part of application No. 09/163,621, filed on Sep. 30, 1998, now Pat. No. 6,000,083.

(51) Int. Cl.⁷ ............................. A46B 13/02; B65D 83/00
(52) U.S. Cl. ........................... 206/362.2; 15/22.1; 15/28; 200/318.2; 206/470
(58) Field of Search .................................. 15/22.1, 22.2, 15/28, DIG. 10; 200/1 B, 43.16, 43.18, 318, 318.1, 318.2; 206/362.2, 320, 470

(56) References Cited

U.S. PATENT DOCUMENTS

| | | | |
|---|---|---|---|
| 2,445,635 | * 7/1948 | Poliakoff | 200/318.2 |
| 3,775,800 | * 12/1973 | Veneziani | 15/28 |
| 4,203,431 | * 5/1980 | Abura | 15/28 |
| 4,897,517 | * 1/1990 | Gundlach | 200/318.1 |
| 5,070,567 | 12/1991 | Holland . | |
| 5,120,225 | * 6/1992 | Amit | 15/22.1 |
| 5,170,525 | * 12/1992 | Cafaro | 15/28 |
| 5,186,627 | 2/1993 | Amit . | |
| 5,274,870 | 1/1994 | Stollman . | |
| 5,341,534 | 8/1994 | Serbinski et al. . | |
| 5,378,153 | 1/1995 | Giuliani et al. . | |
| 5,494,252 | * 2/1996 | Amit et al. | 206/362.2 |
| 5,524,312 | 6/1996 | Tan et al. . | |
| 5,590,434 | 1/1997 | Imai . | |
| 5,732,433 | 3/1998 | Göcking et al. . | |

FOREIGN PATENT DOCUMENTS 2 228 861   12/1990   (GB) .

* cited by examiner

*Primary Examiner*—Randall E. Chin
(74) *Attorney, Agent, or Firm*—Fay, Sharpe, Fagan, Minnich & McKee, LLP

(57) ABSTRACT

An electric toothbrush comprising an elongated body portion and a head including a static portion and a circular portion, a handle, and an angled shaft between the head and the handle. The circular portion rotates or oscillates about an axis normal to a longitudinal axis of the head. The circular portion includes stiff bristles and the static portion includes soft bristles. The elongated body portion is hollow and further includes a motor in the hollow portion, which is operatively connected to the circular portion for rotating or oscillating the circular portion. A switch is operatively connected to the motor to provide momentary and continuous operation of the toothbrush. A worm gear and a pair of step gears are located in the hollow portion. The motor is operatively connected to the worm gear and the step gears are operatively connected to the worm gear and to each other. One of the step gears is offset with respect to a longitudinal axis of the elongated body portion. A shaft which is operatively connected to the offset step gear and to a second end to the circular portion. A battery is located within the hollow section for powering the motor.

4 Claims, 9 Drawing Sheets

ELECTRIC TOOTHBRUSH

This application is a continuation-in-part of application Ser. No. 09/163,621, filed on Sep. 30, 1998 now U.S. Pat. No. 6,000,083.

BACKGROUND OF THE INVENTION

The present invention relates generally to electric toothbrushes. More particularly, it relates to an improved battery powered toothbrush.

The benefits of brushing one's teeth using motorized toothbrushes are well known, and motorized movement in toothbrushes has been the subject of much recent innovation and design activity. Also, the commercial market has seen the introduction, over the last several years, of many different types of motorized toothbrushes. However, an examination of the available technology shows a tendency toward increasingly complex, expensive, and non-commercially feasible methods of achieving motorized motions in the bristles and heads of toothbrushes to aid in more effectively cleaning one's teeth.

The commercial marketplace has become divided into two price markets. On the higher priced end are some of these more complex motorized toothbrushes that provide various motions to the bristles and brush head. The lower end of the market has become the province of very simple motorized toothbrushes that only vibrate through the use of an offset weight attached to the motor shaft, and which provide very little true additional cleaning benefit with their use, since no vigorous motion is transmitted to the cleaning surface of the brush. The vibrations are also very uncomfortable to the hand and act as a disincentive to brush one's teeth for an adequate time.

Numerous electric toothbrushes have been developed over the years. Some known devices are shown in U.S. Pat. No. 5,070,567; U.S. Pat. No. 5,186,627; U.S. Pat. No. 5,274,870; U.S. Pat. No. 5,341,534; U.S. Pat. No. 5,378,153; and U.S. Pat. No. 5,732,433. The intention of the present invention is to provide a low cost, effective, ergonomically correct, motorized toothbrush wherein the brush includes both a moving circular brush portion and a fixed brush portion. Accordingly it has been considered desirable to develop a new and improved electric toothbrush which would overcome the foregoing difficulties and others while providing better and more advantageous overall results.

SUMMARY OF THE INVENTION

The present invention relates to an electric toothbrush.

More specifically, the electric toothbrush is used in personal hygiene to clean one's teeth and gums using a motorized movement.

In a first preferred embodiment, the electric toothbrush includes an elongated body portion, a brush head attached to a first end of the elongated body portion, a handle attached to a second end of the elongated body portion, and an angled shaft between the brush head and the handle.

The brush head includes a longitudinal axis, a circular portion and a static portion. The circular portion rotates, swivels, gyrates or oscillates about an axis normal to the longitudinal axis of the brush head and is incorporated into the larger brush head. The static portion includes static bristles located on opposite sides of the circular portion. The stiff bristles of the circular portion are slightly recessed in height from the static bristles. This particular arrangement allows for the circular portion to include stiff bristles which will aid in the deep cleaning and plaque removal process, while the stationary bristles would typically consist of softer bristles, so as not to damage the gums.

The brush head has a more traditional larger brush head shape which permits the user to brush his teeth in the typical manner of an up and down fashion, while a motorized circular portion of the brush head cleans more effectively. The design of the brush head allows for inexpensive manufacture and brings effective motorized rotational toothbrushes within the financial reach of a larger portion of the population.

The angled shaft provides an ergonomic benefit that has not been utilized on a motorized toothbrush. The angle is well known for its ergonomic benefit in permitting easier access into the back recesses of the mouth while still contacting the tooth surface.

The elongated body portion includes a hollow portion. The toothbrush is further comprised of a motor within the hollow portion of the elongated body portion. The motor is operably connected to the circular portion of the brush head for rotating or oscillating the stiff bristles on the head. The motor has a longitudinal axis which is coaxial with a longitudinal axis of the elongated body portion.

The hollow portion further includes a simplified gear assembly. The gear assembly includes a worm gear, two step gears and a shaft. The motor is operatively connected to the worm gear. The step gears are operatively connected to the worm gear and to each other. The gear assembly delivers sufficient torque, speed, and battery longevity. The first step gear permits a second matching step gear to be offset with respect to a longitudinal axis of the elongated body portion and placed at the desired angle so that the shaft itself can still be straight, thus losing no power or torque through the added friction of a flexible shaft. The shaft is operatively connected at a first end to the offset step gear and at a second end to the circular portion of the brush head.

The body further includes a switch to allow operation of the unit. The switch includes an actuator button and a metal contact. The switch is manually depressed by pressing a molded actuator button down, which presses against a metal contact, completing the circuit, as in a conventional momentary switch. The switch allows continuous operation, through a ramp design, by depressing and sliding the actuator button forward as in a conventional continuous switch. The forward motion, combined with the molded in ramp, causes the actuator button to move downward, pressing against the metal contact, and completing the circuit. By combining these two functions in one switch, the consumer can try the unit and see its operation prior to purchase, and still operate it continuously once out of the package.

The electric toothbrush can further include a battery located within the hollow portion of the elongated body portion. A slidable, snap-on cover is depressed then released from the end of the handle and opens to expose the hollow portion. The battery is then inserted and then the cover is slid into position and snapped into place.

In a second preferred embodiment, the electric toothbrush includes an elongated body portion, a brush head attached to a first end of the elongated body portion, a handle attached to a second end of the elongated body portion, and an angled shaft between the brush head and the handle.

The brush head includes a longitudinal axis, a circular portion, a static portion, a first end and a second end. The first end of the head is located adjacent the first end of the elongated body portion, and the second end is located opposite the first end. The static portion is located at the first end of the head. The circular portion is located at the second end of the head. The circular portion rotates, swivels, gyrates or oscillates about an axis normal to the longitudinal axis of the brush head and is incorporated into the larger brush head. The circular portion is located at the end of the brush head to facilitate easier access and cleaning of the back of the user's mouth. The static bristles are located adjacent the circular portion. This particular arrangement allows for the circular portion to include stiff bristles which will aid in the deep cleaning and plaque removal process further in the back of the user's mouth, while the stationary bristles would typically consist of a softer bristle, so as not to damage the gums.

One advantage of the present invention is the provision of an electric toothbrush with a brush head with a traditional larger brush head shape to permit the user to brush teeth in an up and down fashion.

Another advantage of the present invention is the provision of an electric toothbrush which is easy and inexpensive to manufacture.

Another advantage of the present invention is the provision of an electric toothbrush with an angled shaft to permit easier access to the back of the user's mouth.

Still another advantage of the present invention is the provision of an electric toothbrush with a static portion and a circular portion that rotates or swivels or oscillates.

Yet another advantage of the present invention is the provision of a circular portion that rotates or reciprocates which is positioned at the end of the brush head to facilitate easier access to the back of the user's mouth.

Yet still another advantage of the present invention is the provision of an electric toothbrush with a switch which allows momentary operation or continuous operation of the toothbrush.

Still other advantages and benefits of the invention will become apparent to those skilled in the art upon a reading and understanding of the following detailed description.

BRIEF DESCRIPTION OF THE DRAWINGS

The invention may take physical form in certain parts and arrangements of parts, preferred embodiments of which will be described in detail in this specification and illustrated in the accompanying drawings which form a part hereof, and wherein.

DETAILED DESCRIPTION OF THE PREFERRED EMBODIMENTS

Figure 1:
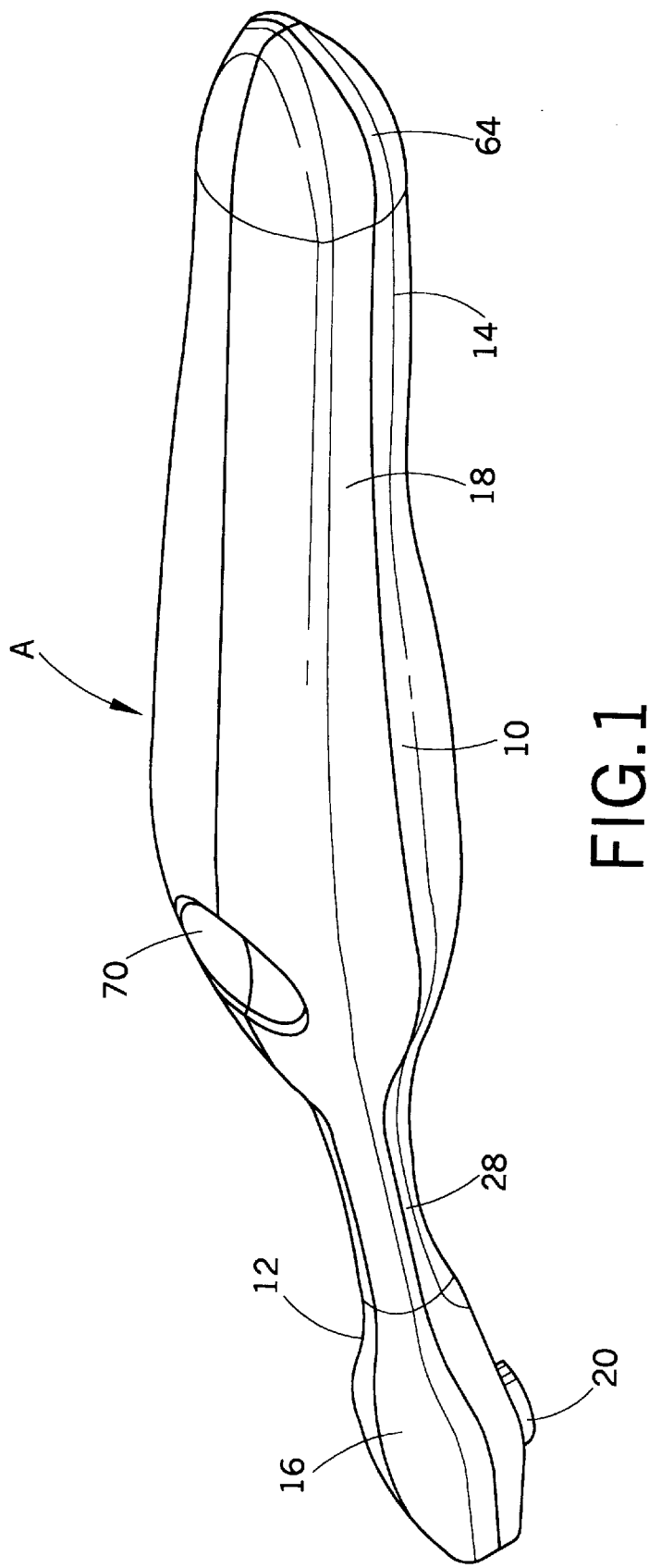
FIG. 1 is a perspective view of the electric toothbrush in accordance with a first preferred embodiment of the present invention.

Referring now to the drawings wherein the showings are for the purposes of illustrating the preferred embodiments of the invention only and not for purposes of limiting same, FIG. 1 shows an electric toothbrush A according to a first preferred embodiment of the present invention. The electric toothbrush can be used for personal hygiene such as brushing one's teeth and gums.

As shown in FIG. 1, the electric toothbrush includes an elongated body portion 10, which has a first end 12 and a second end 14. A head 16 is attached to the first end 12 and a handle 18 is attached to the second end 14.

Figure 2:
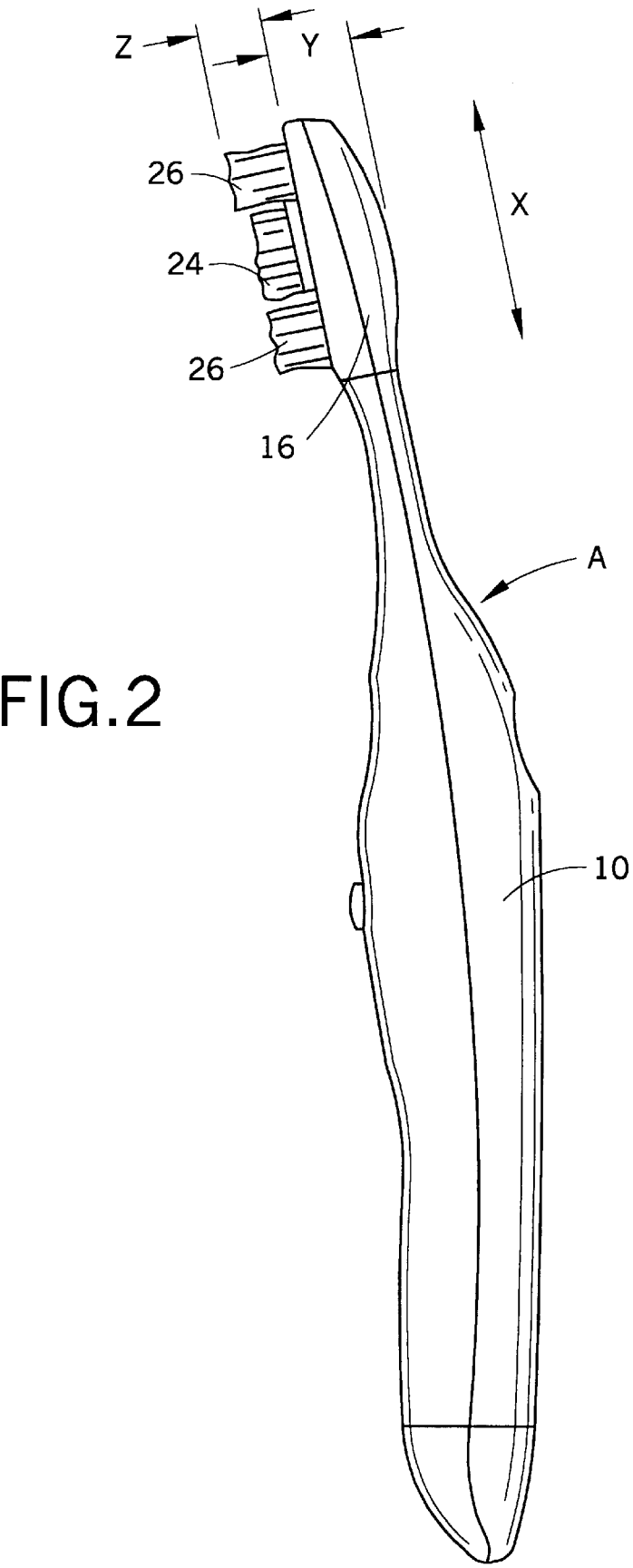
FIG. 2 is a side elevational view of the electric toothbrush of FIG. 1.

The head 16 has a more traditional larger brush head shape which permits the user to brush his teeth in the typical manner of an up and down fashion. As shown on FIG. 2, the length of the head 16, dimension "X", can range from about 0.75 inches to about 1.75 inches. The thickness of the brush head, dimension "Y", can range from about 0.25 inches to about 0.50 inches. The design of the head 16 allows for inexpensive manufacture and assists in bringing effective motorized rotational toothbrushes within the financial reach of a large portion of the population.

Figure 3:
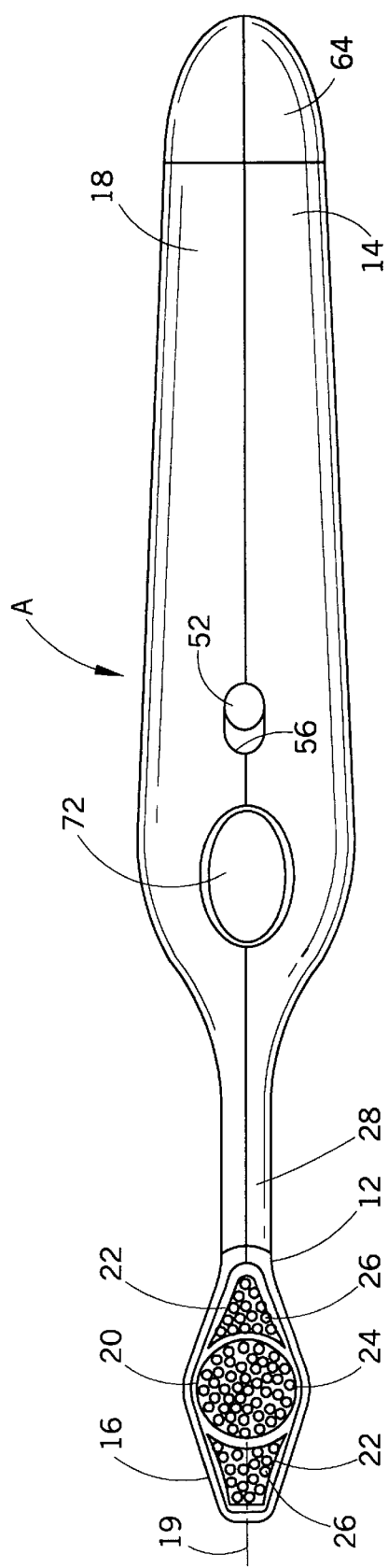
FIG. 3 is a bottom elevational view of the electric toothbrush of FIG. 1.

Referring now to FIG. 3, the head 16 further includes a longitudinal axis 19, a circular or moving portion or brush head 20 and a static portion or brush head 22. The static portion 22 is located on opposite sides of the circular portion 20. The circular portion 20 is located at the center of the brush head 16. The circular portion 20 rotates, swivels, or oscillates about an axis approximately normal to the longitudinal axis 19 of the brush head 16. The circular portion 20 may rotate 360° or partially rotate or oscillate in a back and forth manner.

The circular portion 20 includes stiff bristles 24. The static portion 22 includes soft bristles 26. The stiff bristles 24 are slightly recessed with respect to the soft bristles 26. The stiff bristles 24 aid in the deep cleaning and plaque removal process, while the stationary soft bristles 26 are softer so as to not damage the gums. The thickness of the bristles, dimension "Z", shown in FIG. 2, can range from about 0.25 inches to about 0.75 inches.

Referring again to FIG. 3, the elongated body portion 10 further includes an angled shaft 28, located between the head 16 and the handle 18. The angled shaft 28 provides an ergonomic benefit that has not been utilized on a motorized toothbrush. The angle is well known for its ergonomic benefit in permitting easier access into the back recesses of the mouth while still contacting the tooth surface.

Figure 4:
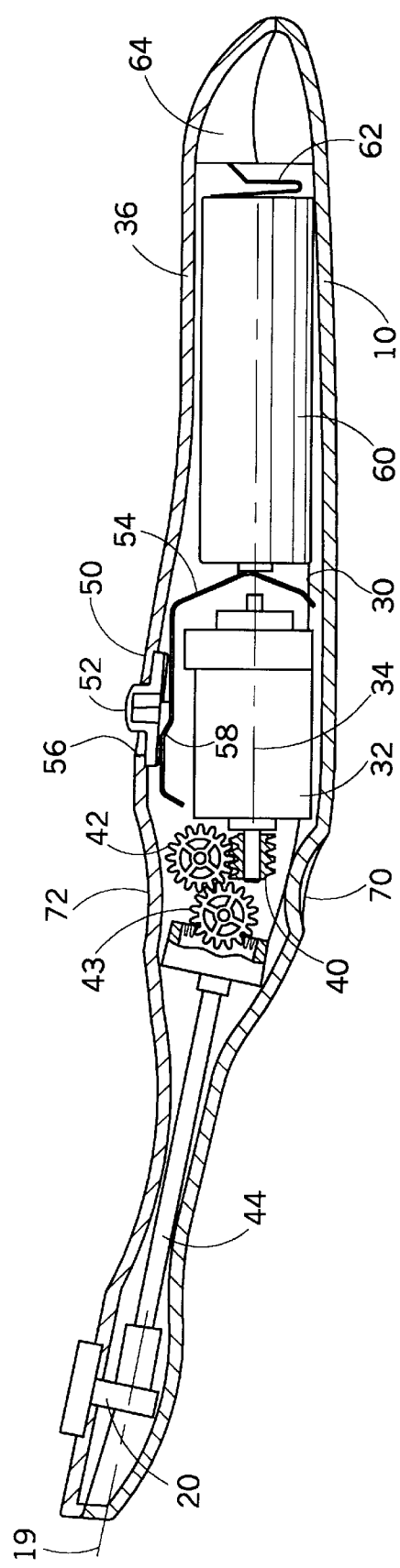
FIG. 4 is a side elevational view in cross section of the electric toothbrush of FIG. 1.
Figure 5:
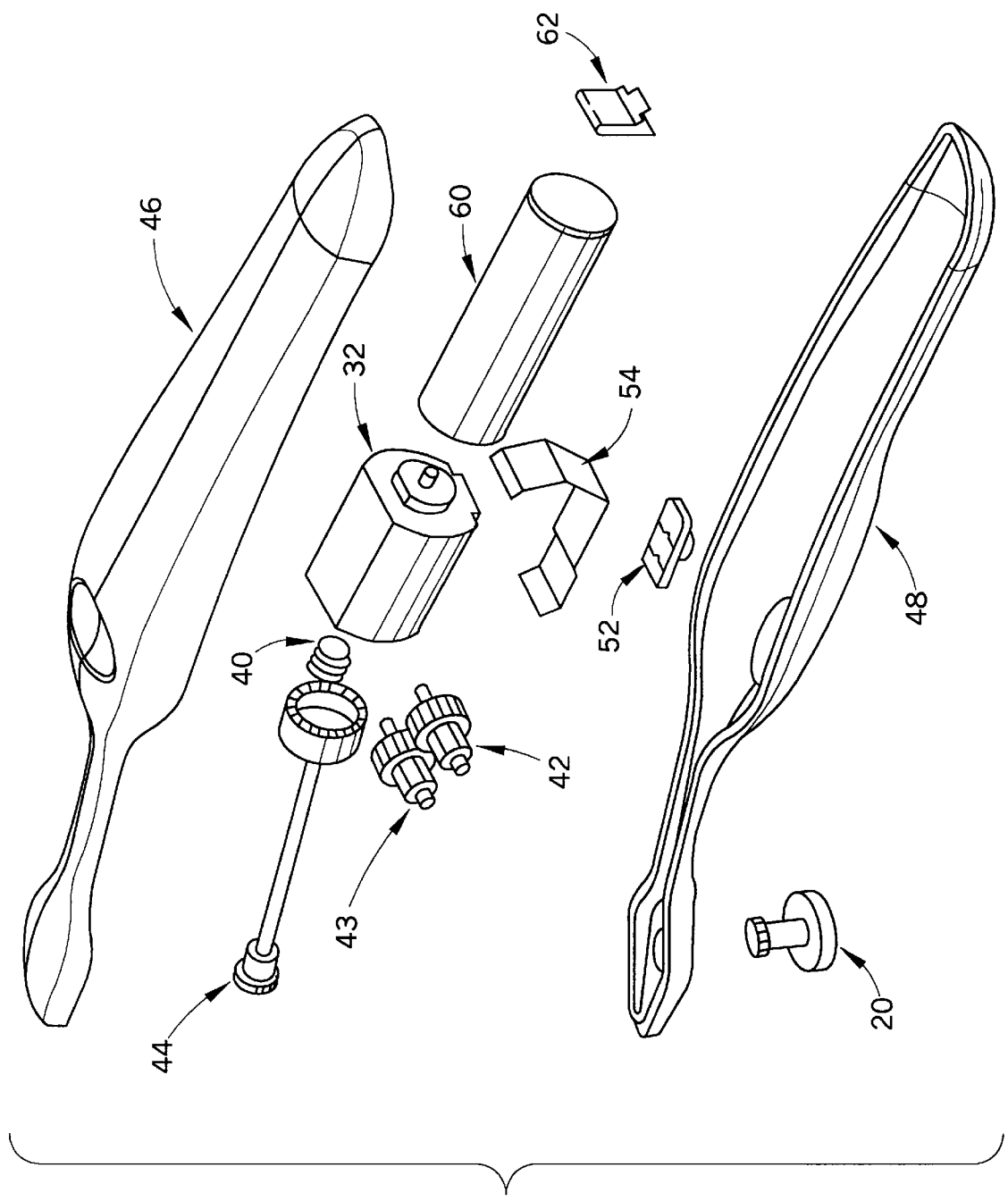
FIG. 5 is an exploded perspective view of the electric toothbrush of FIG. 1.

As shown in FIG. 4 and FIG. 5, the elongated body portion 10 further includes a hollow portion 30 which houses a motor 32. The motor 32 has a longitudinal axis 34 in line with a longitudinal axis 36 of the elongated body portion 10.

To provide power to the circular portion 20 to rotate or oscillate, the motor 32 powers a worm gear 40 and a pair of step gears 42, 43. The motor 32 is operatively connected to the worm gear 40. Step gear 42 is operatively connected to step gear 43 and the worm gear 40.

Figure 6:
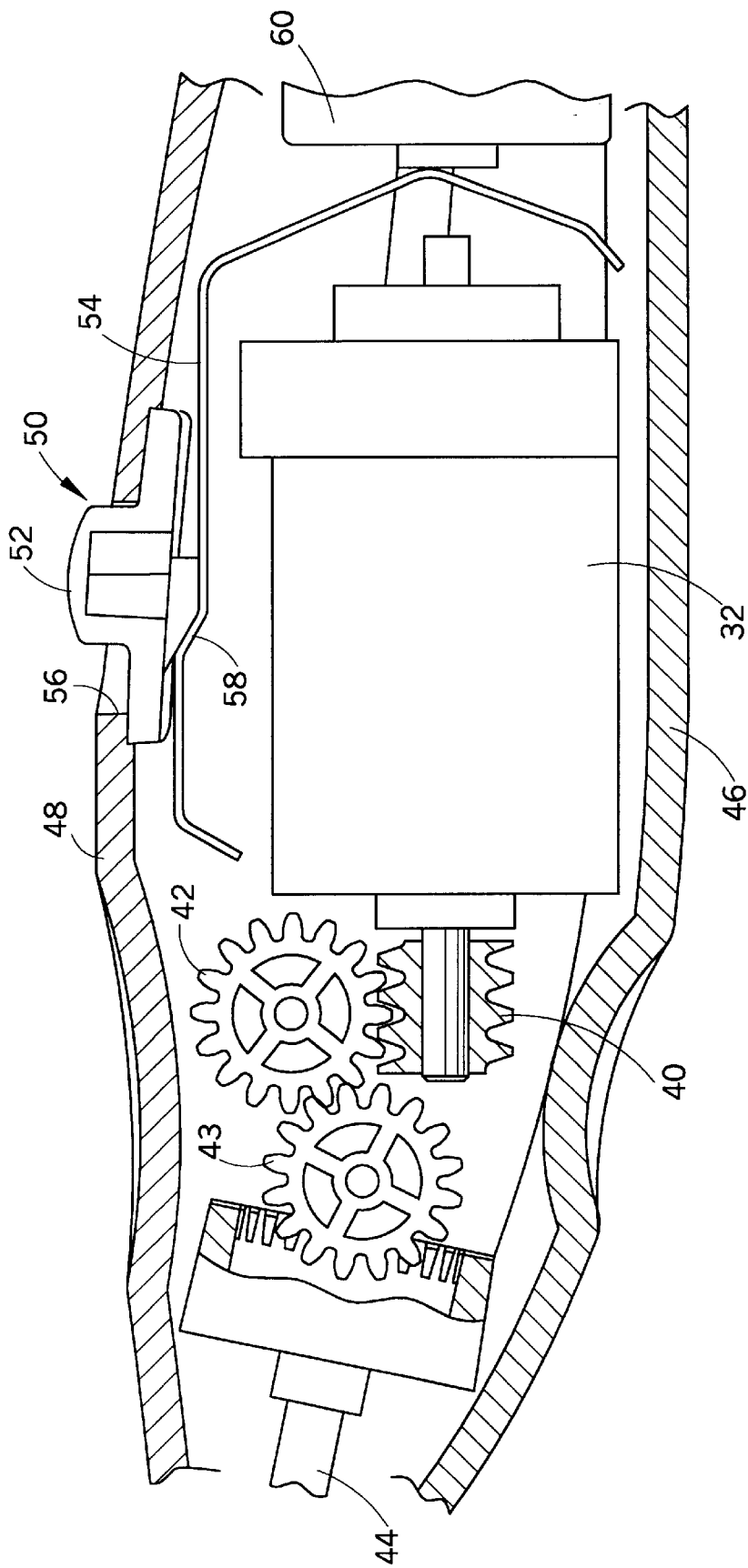
FIG. 6 is an enlarged side elevational view in cross section of the motor and gear assembly of the electric toothbrush of FIG. 1.

As shown in FIG. 4 and FIG. 6, the first step gear 42 permits the matching second step gear 43 to be offset with respect to the longitudinal axis 36 of the elongated body portion 10.

Figure 7:
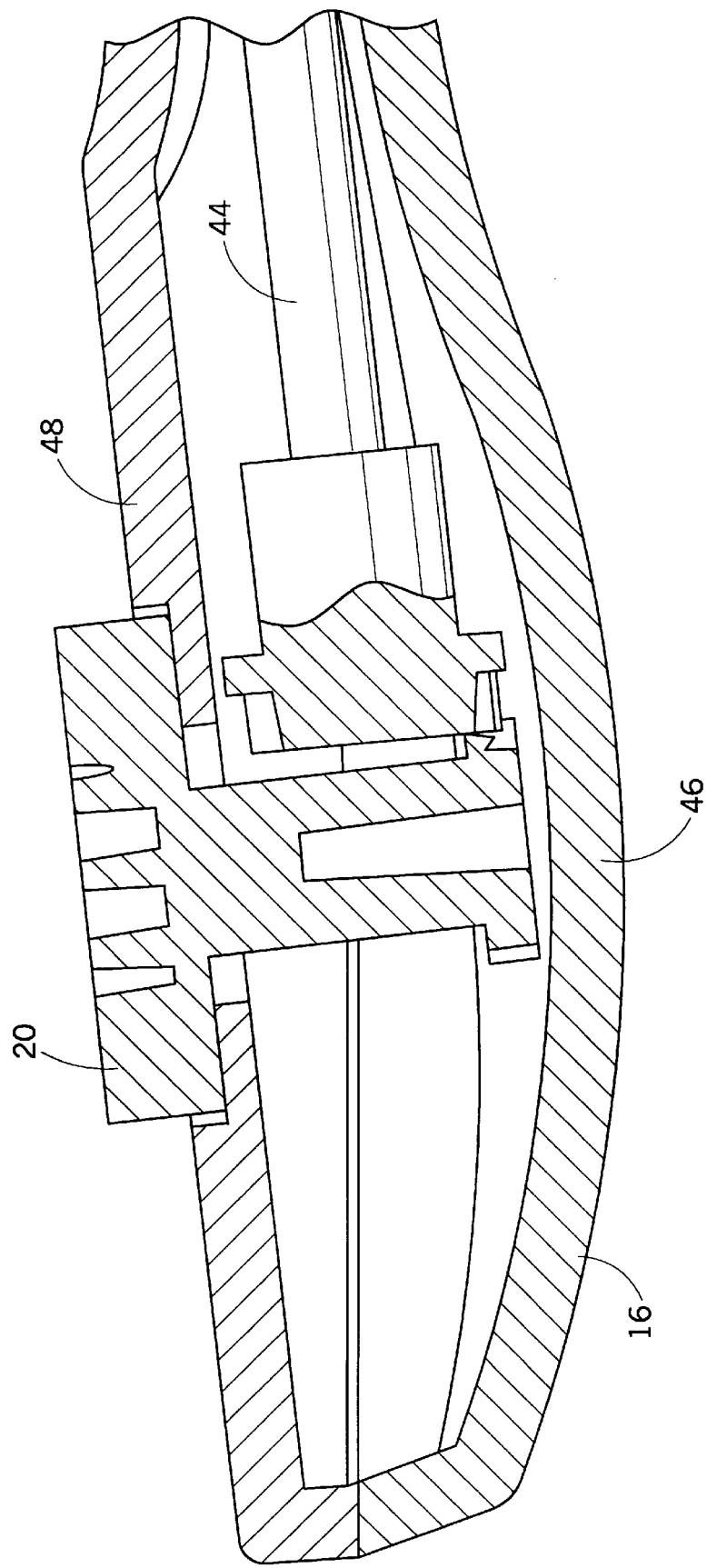
FIG. 7 is an enlarged side elevational view in cross section of the head of the electric toothbrush of FIG. 1.

As shown in FIGS. 4, 6 and 7, a shaft 44 is connected at a first end to the offset step gear 43 and at a second end to the circular portion 20. The second step gear 43 is placed at a desired angle so that the shaft 44 itself can still be straight, thus losing no power or torque through the added function of a flexible shaft.

Referring again to FIG. 5, the motor 32 and gears 40, 42, 43 are housed with an upper housing 46 and a lower housing 48.

Referring again to FIG. 4, a switch 50 is provided to control operation of the electric toothbrush and is operatively connected to the motor 32. The switch 50 includes a molded actuator button 52 and a metal contact 54. The switch 50 is manually depressed by pressing a molded actuator button 52 down, which then presses against a metal contact 54, which completes the circuit and provides momentary operation of the toothbrush. The switch 50 also allows continuous operation through a ramp design, sliding the button 52 forward toward the head 16 to provide for continuous operation. Moving the button 52 forward, combined with a molded in ramp 58 in the metal contact 54, causes the button 52 to move downward, pressing against the metal contact 54 and completing the circuit. The toothbrush then continuously operates until the button 52 is slid back into an off position toward the handle 18 and the button 52 disengages the metal contact 54.

Figure 8:
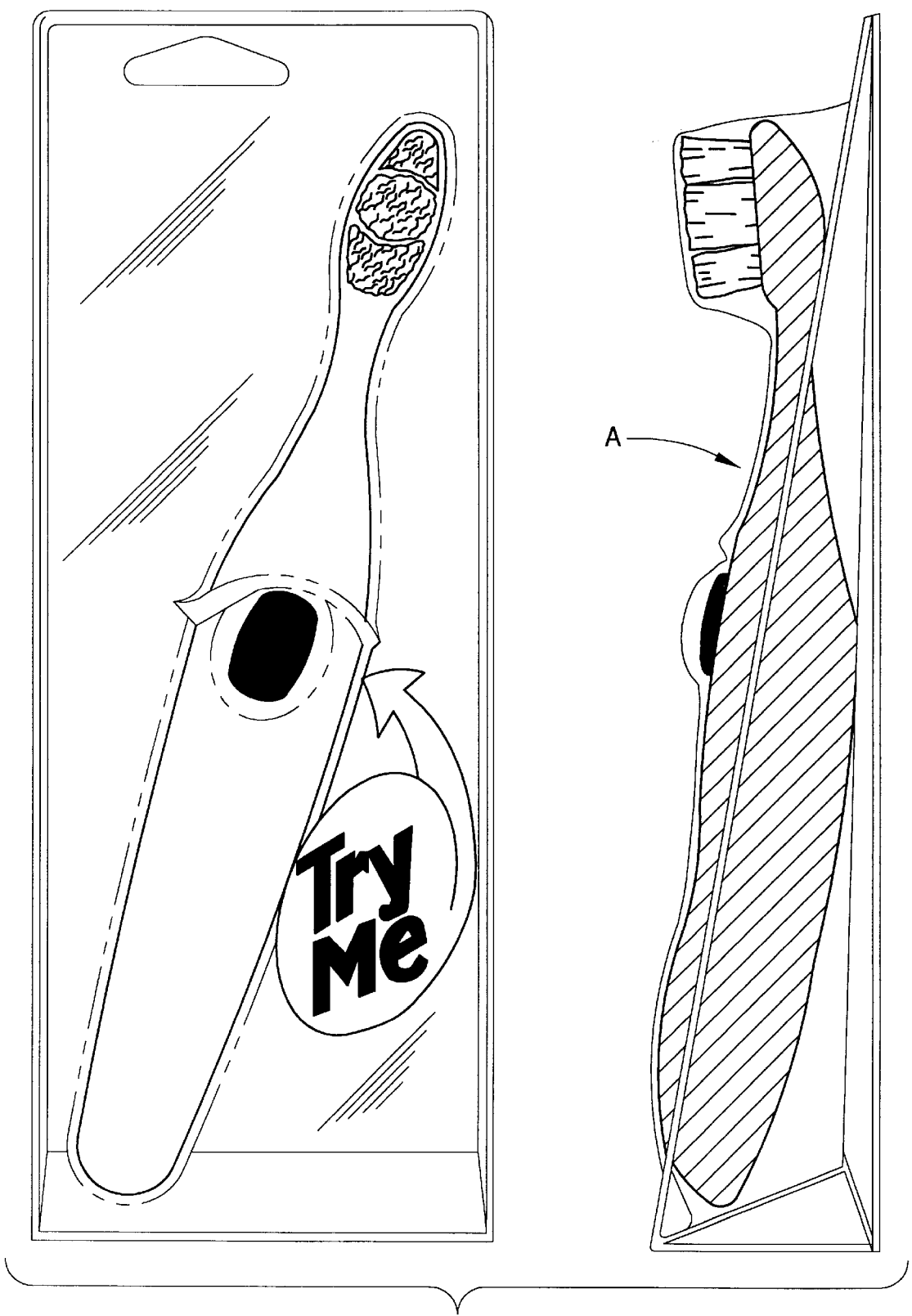
FIG. 8 is a front and side elevational view of the electric toothbrush in packaging.

By combining these two functions in one switch 50, the toothbrush can be packaged in packaging as shown in FIG. 8 where the consumer can depress the button 52 through the packaging and see its operation while still inside the packaging, and then be able to operate it continuously once out of the package. FIG. 8 illustrates one version of the button 52. It should be noted that other sizes and shapes of buttons may be used.

Referring now to FIGS. 4 and 5, a battery 60 is provided within the hollow portion 30 of the elongated body portion 10. A battery terminal or contact 62 is provided for the battery 60. An AA battery can be used as is illustrated in FIG. 4. To install the battery 60 into the hollow portion 30, a slidable snap-on cover 64 is depressed and slid off the end of the handle 18 to expose the hollow portion 30. The battery 60 is inserted, then the cover 64 is slid back on to the housing and snapped into place. The terminal end of the battery 60 is then in contact with the metal contact 54.

If desired, depressions or grip areas 70 and 72 can be molded into the upper and lower housings 46, 48 as shown in FIG. 4. The depressions 70, 72 are used to support a user's thumb and forefinger or other fingers to make using the electric toothbrush easier and more comfortable.

Figure 9:
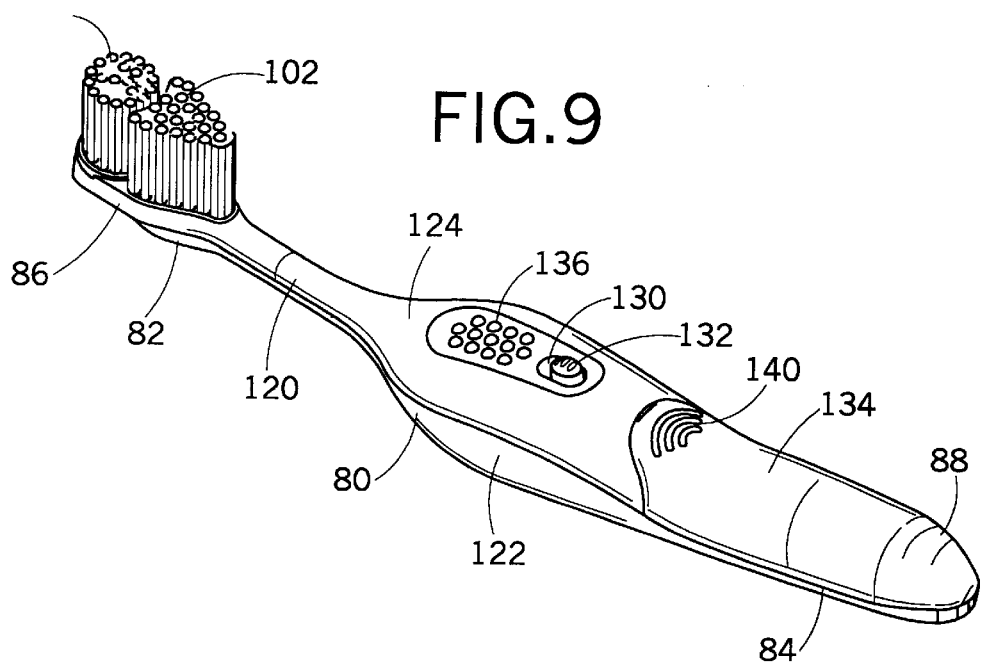
FIG. 9 is a perspective view of the electric toothbrush in accordance with a second preferred embodiment of the present invention.

A second preferred embodiment of the electric toothbrush according to the present invention is shown in FIG. 9.

The electric toothbrush includes an elongated body portion 80 which has a first end 82 and a second end 84. A head 86 is attached to the first end 82 and a handle 88 is attached to the second end 84.

Figure 11:
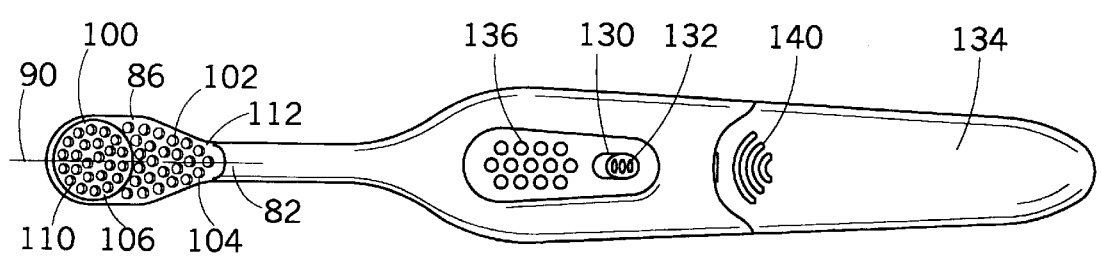
FIG. 11 is a bottom elevational view of the electric toothbrush of FIG. 9.

Referring now to FIG. 11, the head 86 further includes a longitudinal axis 90, a circular portion or brush head 100, a static portion or brush head 102, a first end 104, and a second end 106. The first end 104 is located adjacent the first end 82 of the elongated body portion 80. The second end 106 is located opposite the first end 104. The circular portion 100 is located at the second end 106 of the head 86. The static portion 102 is located at the first end 104 of the head 86 adjacent the circular portion 100. The circular portion 100 rotates, swivels, or oscillates about an axis approximately normal to the longitudinal axis 90 of the brush head 86. The circular portion 100 may rotate 360° or partially rotate or oscillates. The circular portion 100 includes stiff bristles 110. The static portion 102 includes soft bristles 112. The stiff bristles 110 may be slightly recessed with respect to the soft bristles 112. The stiff bristles 110 aid in the deep cleaning and plaque removal process, while the stationary soft bristles 112 are softer so as to not damage the gums.

Figure 10:
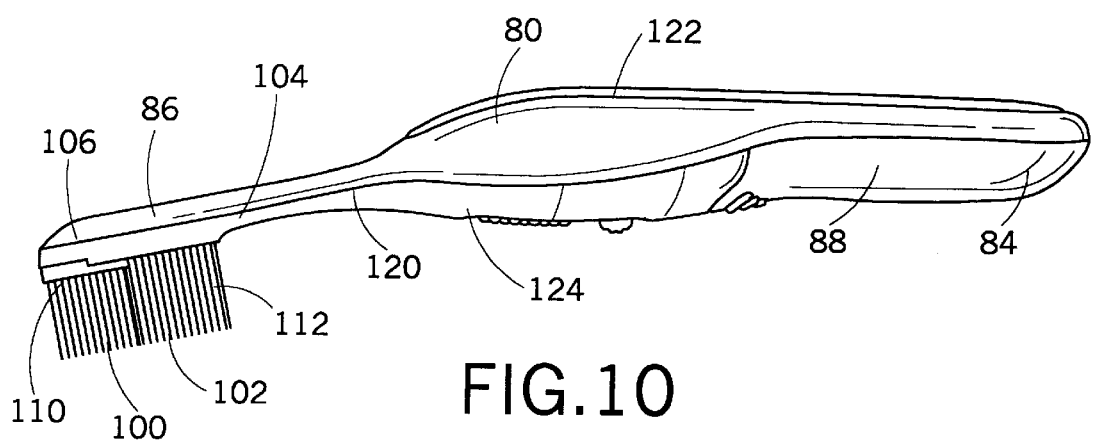
FIG. 10 is a side elevational view of the electric toothbrush of FIG. 9.

Referring to FIG. 10, the elongated body portion 80 further includes an angled shaft 120, an upper housing 122, and a lower housing 124. The angled shaft 120 is located between the head 86 and the handle 88. The angled shaft 120 provides an ergonomic benefit that has not been utilized on a motorized toothbrush.

The elongated body portion 80 of the second preferred embodiment also includes a hollow portion 30 which houses a motor 32 as shown in FIGS. 4–7 for the first preferred embodiment. The motor 32 provides power to the circular portion 100 to rotate or oscillate. The interior of the elongated body portion 80 is identical to that shown in FIGS. 4–7 with the exception of the location of the circular portion 100. As described above, the circular portion 100 is located at the second end 106 of the brush head 86. The second preferred embodiment also has a worm gear 40 and a pair of step gears 42, 43 as shown in FIGS. 4 and 6. The motor 32 powers the worm gear 40 and the pair of step gears 42,43. The step gear 42 permits the matching step gear 43 to be offset with respect to the longitudinal axis of the elongated body portion 80.

As shown in FIGS. 4, 6, and 7, a shaft 44 is connected at a first end to the offset step gear 43 and at a second end to the circular portion 100. The second step gear 43 is placed at a desired angle so that the shaft 44 can still be straight, thus losing no power or torque through the added function of a flexible shaft.

Referring again to FIG. 9, a switch 130 is provided to control operation of the electric toothbrush and is operatively connected to the motor 32. The switch 130 includes a molded actuator button 132. The switch 130 is manually depressed by pressing a molded actuator button 132 down, which then presses against a metal contact 54, which completes the circuit and provides momentary operation of the toothbrush. The operation of the switch 30 is identical to that shown in FIGS. 4 and 6 and as described for the first preferred embodiment. The switch 130 also allows continuous operation through a ramp design, sliding the button 132 forward toward the head 86 to provide for continuous operation. The toothbrush then continuously operates until the button 132 is slid back into an off position toward the handle 88 and the button 132 disengages the metal contact 54.

As shown in FIGS. 4 and 5 for the first preferred embodiment, the second preferred embodiment also has a battery 60 with a battery terminal or contact 62 provided within the hollow portion 30 of the elongated body portion 80. To install the battery 60 into the hollow portion 30, a slidable snap-on cover 134 (shown in FIGS. 9–11) is depressed and slid off the end of the handle 88 to expose the hollow portion 30. The battery 60 is inserted, then the cover 134 is slid back on to the housing and snapped into place.

If desired, raised grip areas 136 can be molded into the lower housing 124 as shown in FIG. 9 and FIG. 11. The raised portions 136 are used to support a user's thumb and forefinger or other fingers to make using the electric toothbrush easier and more comfortable. Raised portion 140 may also be molded onto the snap-on cover 134 to aid in gripping the cover with one's thumb and removing the cover from the handle 88.

The electric toothbrush of the second preferred embodiment can also be packaged in packaging as shown in FIG. 8 as shown for the first preferred embodiment where the consumer can depress the button 132 through the packaging and see its operation while still inside the packaging, and then be able to operate it continuously once out of the packaging.

The invention has been described with reference to the preferred embodiments. Obviously, modifications and alterations will occur to others upon a reading and understanding of this specification. It is intended to include all such modifications and alterations insofar as they come within the scope of the appended claims or the equivalents thereof.

What is claimed is:

1. An electric toothbrush comprising:

packaging for containing the toothbrush;

an elongated body portion having opposed first and second ends, a hollow portion and a longitudinal axis;

a head attached to said first end, wherein said head includes a moving portion;

a motor located within said hollow portion of said elongated body portion, said motor being configured to produce a moving motion for the moving portion;

a shaft operatively connected to said motor at a first end and to the moving portion at a second end;

a handle attached to said second end of said elongated body portion; and a switch which is operably connected to said motor, wherein said switch is actuated in a first manner to provide momentary operation of said toothbrush when the toothbrush is within the packaging, and is actuated in a second manner to provide continuous operation of said toothbrush when the toothbrush is out of the packaging.

2. The electric toothbrush of claim 1 further comprising a head which has a traditional brush head shape having dimensions of 0.75 inches to 1.75 inches in length and 0.25 inches to 0.50 inches in thickness.

3. The toothbrush as defined in claim 1 wherein when said switch is actuated in a first manner, the switch is depressed to provide the momentary operation.

4. The toothbrush as defined in claim 1 wherein when said switch is actuated in a second manner, the switch is depressed and slid in a slot in said elongated body portion.

* * * * *